United States Patent
Shuk et al.

(10) Patent No.: US 11,668,687 B2
(45) Date of Patent: *Jun. 6, 2023

(54) COMBUSTION ANALYZER WITH DUAL CARBON MONOXIDE AND METHANE MEASUREMENTS

(71) Applicant: Rosemount Inc., Shakopee, MN (US)

(72) Inventors: Pavel Shuk, Copley, MN (US); Chad M. McGuire, Shakopee, MN (US)

(73) Assignee: Rosemount Inc., Shakopee, MN (US)

( * ) Notice: Subject to any disclaimer, the term of this patent is extended or adjusted under 35 U.S.C. 154(b) by 583 days.

This patent is subject to a terminal disclaimer.

(21) Appl. No.: 16/587,805

(22) Filed: Sep. 30, 2019

(65) Prior Publication Data

US 2021/0096116 A1 Apr. 1, 2021

(51) Int. Cl.
  *G01N 33/00* (2006.01)
  *G05B 15/02* (2006.01)

(52) U.S. Cl.
  CPC ..... *G01N 33/0031* (2013.01); *G01N 33/0006* (2013.01); *G01N 33/0063* (2013.01); *G05B 15/02* (2013.01)

(58) Field of Classification Search
  CPC .... G01N 31/12; G01N 25/50; G01N 33/0067; G01N 33/0065; G01N 33/0063;
  (Continued)

(56) References Cited

U.S. PATENT DOCUMENTS 4,362,269 A 12/1982 Rastogi et al.
5,265,417 A * 11/1993 Visser ............... F01N 11/00
  60/274

(Continued)

FOREIGN PATENT DOCUMENTS

EP 1962088 B1 12/2009
EP 3077643 B1 * 10/2019 ............... F23C 9/06
(Continued)

OTHER PUBLICATIONS

International Search Report and Written Opinion for International Patent Application No. PCT/US2020/052189, dated Jan. 12, 2021, 11 pages.

(Continued)

*Primary Examiner* — John Fitzgerald
*Assistant Examiner* — Truong D Phan
(74) *Attorney, Agent, or Firm* — Christopher R. Christenson; Kelly, Holt & Christenson, PLLC

(57) ABSTRACT

A combustion analyzer configured to simultaneously detect the concentrations of oxygen, carbon monoxide and methane in a combustion process is provided. The combustion analyzer includes an oxygen sensor configured to detect the oxygen in the combustion process and generate a first sensor signal indicative of the concentration of oxygen in the combustion process. The combustion analyzer further includes a dual carbon monoxide-methane sensor configured to operate at approximately 600° C. and provide a second sensor signal indicative of methane concentration and at approximately 300° C. to selectively provide a third sensor signal indicative of carbon monoxide concentration. The combustion analyzer finally includes a controller configured to receive the sensor signals, determine the concentration of oxygen and generate a carbon monoxide concentration output and a methane concentration output based on the dual carbon monoxide-methane sensor signals and the concentration of oxygen.

18 Claims, 14 Drawing Sheets

(58) Field of Classification Search
CPC ............ G01N 33/007; G01N 33/0006; G01N 33/0073; G01N 33/004; G01N 25/22; G01N 25/36; G01N 33/0004; G01N 33/0031; G01N 25/20; G01M 15/102; G05B 15/02; F23N 5/003; F23N 5/006; F23N 5/02; F23N 5/18; F23N 5/26; F23N 2900/05001; F23N 2900/05002; F23N 2900/05003; F23N 2900/05005; F23N 2900/00

See application file for complete search history.

(56) References Cited

U.S. PATENT DOCUMENTS

| | | | |
|---|---|---|---|
| 6,070,450 A * | 6/2000 | Takao | G01N 33/004 73/23.31 |
| 6,368,479 B1 | 4/2002 | Yokota et al. | |
| 11,346,554 B2 * | 5/2022 | Shuk | G01N 33/0047 |
| 2013/0302738 A1 | 11/2013 | Rennie et al. | |
| 2017/0003246 A1 | 12/2017 | Shuk et al. | |

FOREIGN PATENT DOCUMENTS

| | | | | |
|---|---|---|---|---|
| GB | 2518155 A | * | 3/2015 | ......... G01N 33/0009 |
| WO | WO-2008045568 A2 | * | 4/2008 | ........ H01M 8/04216 |

OTHER PUBLICATIONS

Jonas, T.A. and Walsh, P.T., 1988. Flammable gas detection. Platinum Metals Review, 32(2), pp. 50-60.

Sears, W.M., Colbow, K. and Consadori, F., 1989. General characteristics of thermally cycled tin oxide gas sensors. Semiconductor science and technology, 4(5), p. 351.

Sears, W.M., Colbow, K., Slamka, R. and Consadori, F., 1990. Selective thermally cycled gas sensing using fast Fourier-transform techniques. Sensors and Actuators B: Chemical, 2(4), pp. 283-289.

Chintoanu, M., Ghita, A., Aclu, A., Pitl, G., Costiug, S., Cadar, S., Ferenczi, L. and Cordas, E., 2006, May. Methane and carbon monoxide gas detection system based on semiconductor sensor. In 2006 IEEE international conference or automation, quality and testing, robotics (vol. 2, pp. 208-211). IEEE.

Tate, J.D., Le, L.D., Knittel, T. and Cowie, A., 2010. Advanced Combustion Diagnostics and Control for Furnaces, Fired Heaters and Boilers (No. DOE/GO/16093). Dow Chemical Company.

Office Action dated Oct. 14, 2021, for U.S. Appl. No. 16/587,222, 13 pages.

First Office Action dated Apr. 19, 2022, for Chinese Patent Application No. 202011069774.1, 25 pages including English translation.

First Office Action for Japanese Patent Application No. 2022-519986, dated Apr. 4. 2023, 15 pages including English translation.

* cited by examiner

COMBUSTION ANALYZER WITH DUAL CARBON MONOXIDE AND METHANE MEASUREMENTS

BACKGROUND

The process industries often rely on energy sources that include one or more combustion processes. Such combustion processes include operation of a furnace or boiler to generate steam or to heat a feedstock liquid. While combustion provides relatively low-cost energy, combustion efficiency is sought to be maximized. In addition, flue gases from industrial processes exiting smoke stacks are often regulated, and the amount of dangerous gases often must be minimized. Accordingly, one goal of the combustion process management industry is to maximize combustion efficiency of existing furnaces and boilers, which inherently also reduces the production of greenhouse and other regulated gases. Combustion efficiency can be optimized by maintaining the ideal level of oxygen in the exhaust or flue gases coming from such combustion processes.

In-situ or in-process analyzers are commonly used for the monitoring, optimization, and control of the combustion process. Typically, these analyzers employ sensors that are heated to relatively high temperatures and are operated directly above, or near, the furnace or boiler combustion zone. Known process combustion analyzers typically employ a zirconium oxide sensor disposed at an end of a probe that is inserted directly into a flue gas stream. As the exhaust, or flue gas, flows into the sensor, it diffuses into proximity with the sensor. The sensor provides an electrical signal related to the amount of oxygen present in the gas.

SUMMARY

A combustion analyzer configured to simultaneously detect the concentrations of oxygen, carbon monoxide and methane in a combustion process is provided. The combustion analyzer includes an oxygen sensor configured to detect the oxygen in the combustion process and generate a first sensor signal indicative of the concentration of oxygen in the combustion process. The combustion analyzer further includes a dual carbon monoxide-methane sensor configured to operate at approximately 600° C. and provide a second sensor signal indicative of methane concentration and at approximately 300° C. to selectively provide a third sensor signal indicative of carbon monoxide concentration. The combustion analyzer finally includes a controller configured to receive the sensor signals, determine the concentration of oxygen and generate a carbon monoxide concentration output and a methane concentration output based on the dual carbon monoxide-methane sensor signals and the concentration of oxygen.

DETAILED DESCRIPTION

Figure 1:
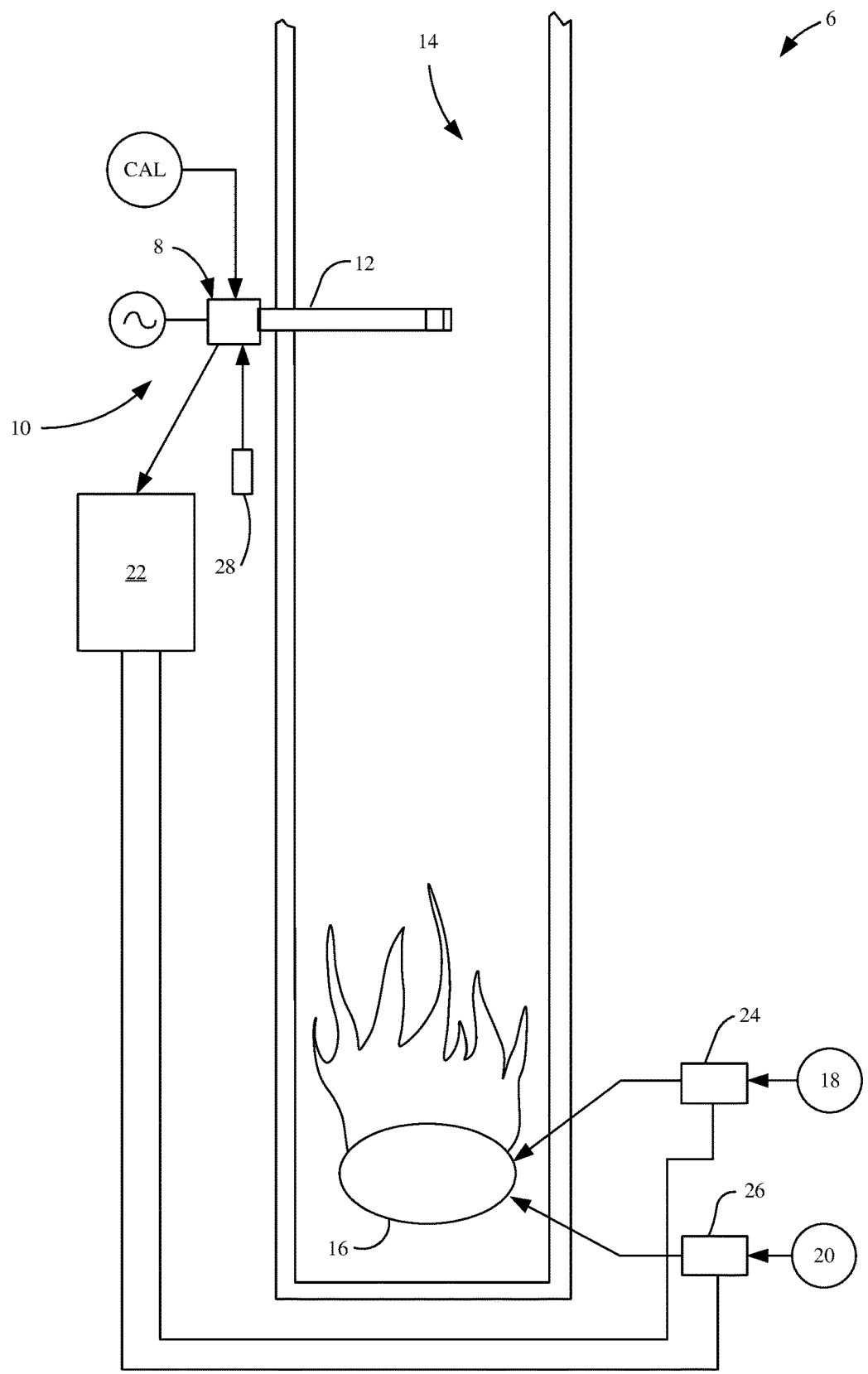
FIG. 1 is a diagrammatic view of an in-situ combustion analyzer with which examples of the present invention are particularly applicable.

Zirconia-based electrochemical oxygen sensors are widely used in industrial applications for oxygen measurements. The electrochemical oxygen sensor works at elevated temperatures, for example approximately 600-800° C., and measure the oxygen excess remaining after combustion. The response of the sensor to differential oxygen concentrations with fixed partial pressure on the reference electrode, e.g. using air, can be calculated using the Nernst equation:

$$EMF + \frac{RT}{4F} \ln \frac{P_{process}}{P_{ref}} + C = 0.0496 * T * \log \frac{P_{process}}{P_{ref}} + C \quad \text{Equation 1}$$

where C is the constant related to the reference/process sides temperature variation and thermal junctions in the oxygen probe, R is the universal gas constant, T is the process temperature in K and F is the Faraday constant.

Electrochemical zirconia oxygen sensors are robust and can work for years in the combustion environment. In perfect combustion, oxygen and fuel combine in an ideal ratio producing primarily carbon dioxide and water with traces of other gases coming from fuel impurities and nitrogen oxidation, like sulfur dioxide, and nitrogen oxides. This stoichiometric point with the highest efficiency would be very difficult to achieve in actual combustion because of imperfect fuel/air uniformity, the fuel energy density, and fuel/air flow variation. Typical flue gas oxygen excess concentration is between approximately 2-3% for gas burners and approximately 2-6% for boilers and oil burners. The most efficient combustion, which typically occurs between 0.75% and 2.0% oxygen concentration, is very difficult to achieve and maintain using just oxygen detection and control in the combustion process. Any leaks on the boiler or any other part of the combustor's wall would allow additional oxygen penetration, compromising the oxygen concentration measurement and disrupting combustion control.

While a degree of combustion control can be accomplished with oxygen measurement alone, combustion efficiency and stability can be improved with the concurrent measurement of carbon monoxide, employed additionally in the combustion analyzer. Carbon monoxide is formed in the combustion process when the combustion of hydrocarbon fuel is not mixed with sufficient oxygen or when a combustion burner is failing or malfunctioning. Thus, the concentration of carbon monoxide can be used as an indicator of incomplete or fuel-rich combustion. The presence of more than trace carbon monoxide concentrations can be used as a diagnostic, indicating burner malfunction. Whereas, operation at near trace carbon monoxide levels of about 100-200 ppm (parts per million) and a slight amount of excess air would indicate that the combustion conditions are near the stoichiometric point with the highest efficiency.

At combustion startup, or in the event of a burner malfunction or blowout, the combustor can be filled with an explosive mixture faster than the response time of normal flame sensors installed in a combustion process. This can potentially lead to an explosive result, possibly causing injury or loss of life and loss of capital and operating revenue. Imperfect gas mixing and flue gas stratification can cause dangerous conditions at start-up. The presence and concentration of methane in the combustion process can be used as a diagnostic, indicating that a dangerous condition can be present. In particular, when the concentration of methane remains high, it is an indication that ignition did not occur. To detect and help avoid this condition a methane sensor is required.

A combustion analyzer providing a methane measurement, in addition to oxygen and carbon monoxide, would provide an extra safety feature for control and diagnostics of the combustion process. Available combustion analyzers with oxygen sensors, based on electrochemical zirconia technology, measure the remaining oxygen excess in the combustion process with the sensor output depending logarithmically on the oxygen concentration according to the Nernst equation (shown above). Carbon monoxide formed in the combustion process near the stoichiometric point will be measured qualitatively by a catalytic calorimetric carbon monoxide sensor employed in the combustion analyzer and will indicate a carbon monoxide breakthrough in the combustion process. Known combustion analyzers are either not sensitive to methane (e.g. calorimetric sensors) or are equally sensitive to carbon monoxide and methane and not highly reliable in challenging and severe combustion environments (e.g. mixed potential sensors).

A combustion analyzer capable of measuring oxygen, carbon monoxide, and methane simultaneously is needed. Such a combustion analyzer is provided herein. In one example, an optimized calorimetric catalytic sensor is employed in a combustion analyzer providing simultaneous carbon monoxide and methane measurements separated by an oxygen sensor providing an oxygen measurement.

In combustion process regulation at 1.0-6.0% oxygen concentration in flue gas, carbon monoxide is the first to breakthrough in incomplete combustion. Methane or hydrocarbons are only present before ignition in fuel-air mixture with approximately 20.0% oxygen concentration. In other words, the presence of methane indicates that the fuel/air combination has not been ignited, thus indicating a dangerous buildup of explosive gases in the combustion process.

In one example, the optimized calorimetric catalytic sensor (described above) would be sensitive to ppm carbon monoxide concentration and percentage methane concentration and would be calibrated with approximately 1000 ppm carbon monoxide (greater than or equal to 0 ppm-less than 1000 ppm carbon monoxide range) and approximately 5.0% methane (greater than or equal to 0%-less than or equal to 5.0% methane range). In another example, calibration algorithms implemented in software can be used to calculate and display carbon monoxide concentration in combustion control mode with oxygen concentration less than 10.0% (greater than or equal to 0%-less than 10.0% oxygen concentration range) and methane concentration with oxygen concentration approximately 20.0% (greater than or equal to 10.0%-less than or equal to 20.0% oxygen range).

FIG. 1 is a diagrammatic view of an in-situ process combustion analyzer with which examples of the present invention are particularly applicable. Combustion analyzer 10 can be implemented with commercially available combustion analyzers, for example, a Model OCX 8800 combustion analyzer available from Rosemount Inc., of Shakopee, Minn. (an Emerson company). Analyzer 10 can include a communication module 8 (e.g. a transmitter) configured to communicate with components of installation 6. In one example, transmitter 8 communicates wirelessly, for example via the Bluetooth protocol. In another example, communication module 8 communicates through a wired loop (not shown). In another example, communication module 8 communicates to remote devices (not shown in FIG. 1) such as, but not limited to, field communicators, personal computers, a control center, handheld devices, or various user interfaces. In another example, communication module communicates according to the 4-20 mA HART communication protocol, or the FOUNDATION Fieldbus digital communication protocol. In one example, analyzer 10 has a process temperature range of up to 1427° C.

Analyzer 10, in one example, includes sampling pipe 12 that is substantially disposed within stack or flue 14 and measures oxygen, carbon monoxide and/or methane concentration related to the combustion process occurring at burner 16. In one example, analyzer 10 mounts to a duct, operably coupled to the flue or stack. In one example, burner 16 is operably coupled to a source of air or oxygen source 18 and source 20 of combustion fuel. Each of sources 18 and 20 can be controllably coupled to burner 16 in order to control the combustion process. Analyzer 10 measures the amount of oxygen, carbon monoxide and/or methane in the combustion process and provides an indication of the oxygen, carbon monoxide and/or methane concentration to combustion controller 22. Controller 22, which can include one or more microprocessors, controls one or both of valves 24 and 26 to provide closed loop combustion control. In one example, controller 22 operates automatically, such that an indication of too much or too little oxygen, carbon monoxide and/or methane in the combustion process results in a change in the amount of oxygen or fuel provided to the combustion chamber. In another example, controller 22 provides an indication of the measured concentrations to various user interfaces. In another example controller 22 triggers an alarm or an alert providing an indication of a status of the combustion process (or installation 6) or providing an indication that an action should be taken.

Installation 6 can also include gas assembly 28, operably connected to analyzer 10. In one example, gas assembly 28 provides calibration gases (e.g. gases having known concentrations) to analyzer 10 during calibration operations. In one example, gas assembly 28 can provide three calibration (or test) gases to analyzer 10. In one example, the three gases are a low oxygen test gas, a high oxygen test gas and a carbon monoxide test gas. In another example, gas assembly 28 can provide methane test gas to analyzer 10. In another example, gas assembly 28 can include an air source configured to provide air to analyzer 10, for example, reference air (e.g. for purposes of calibration and measurement), or instrument air (e.g. eductor air and/or dilution air). Gas assembly 28 can include a number of solenoids and flowmeters configured to provide and control test gas and air flow to analyzer 10.

Figure 2:
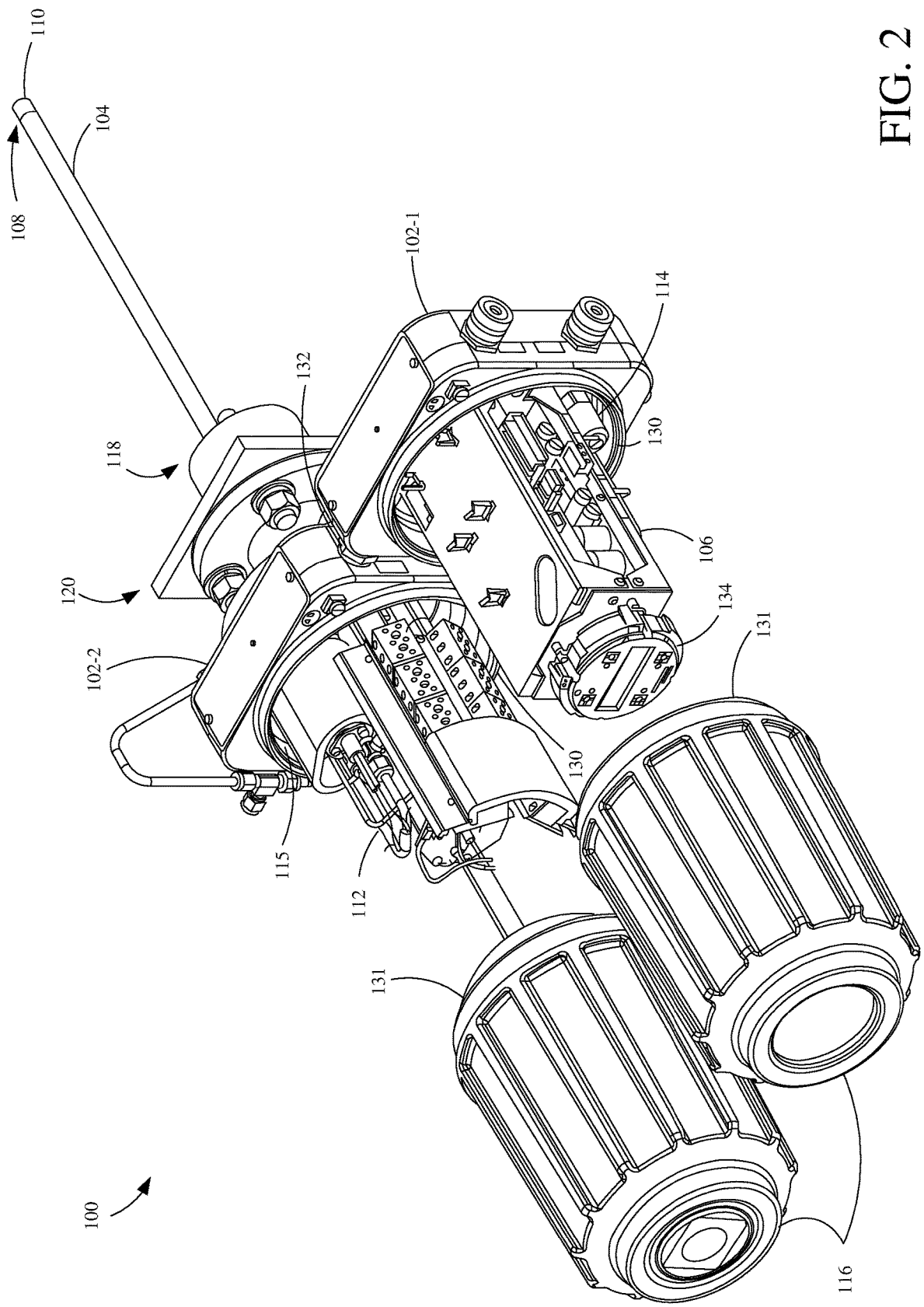
FIG. 2 is a diagrammatic perspective view of a combustion analyzer with which examples of the present invention are particularly applicable.

FIG. 2 is a diagrammatic perspective view showing one example of a combustion analyzer with which examples of the present invention are particularly applicable. Analyzer 100 includes electronics housing 102-1 and sensor housing 102-2, collectively referred to herein as housing 102, sampling pipe 104, and electronics 106 with protective covers 116. Sampling pipe 104 has a distal end 108 where an aperture 110 is disposed. Sampling pipe may comprise various materials, for example, but not limited to, metal alloys (e.g. nickel-chromium alloy and/or Inconel 600), steel (e.g. 316 stainless steel), ceramic, and various other materials suitable for high-temperature process environments. The aperture 110 allows flue gas to pass through sampling pipe 104 to sensors 112 where concentration measurements of oxygen, carbon monoxide and/or methane are taken.

Housing 102 has a chamber 114 that is sized to house electronics 106. Housing 102 has a chamber 115 that is sized to house sensors 112. Additionally, housing 102 can include internal threads 130 that are adapted to receive and mate with external threads 131 of cover 116 to make a hermetic seal. In other examples, covers 116 may be coupled to housing 102 through other fasteners (e.g. bolts) or through a variety of other coupling techniques, for example, a weld. Additionally, housing 102 can include aperture 132 (e.g. a bore) therethrough allowing electrical interconnection between electronics 106 and measuring cells or sensors 112 disposed within chamber 115.

Sensors 112, in one example, include an oxygen sensor and a dual carbon monoxide-methane sensor configured to sense and provide measurements of oxygen, carbon monoxide and/or methane. In one example, sensors 112 are configured to simultaneously sense and/or measure oxygen, carbon monoxide and/or methane. In another example, sensors 112 include an electrochemical oxygen sensor based on zirconia solid electrolyte and a dual carbon monoxide-methane calorimetric catalytic sensor configured to measure carbon monoxide and/or methane. In some examples, the catalysts used on the calorimetric catalytic sensor can include noble metals, e.g. platinum or metal oxides, for example, Hopcalite, or any other suitable catalysts for the detection and measurement of gases in a combustion process. In another example, sensors 112 can include one or more resistance temperature detectors. In another example, sensors 112 can include one or more temperature detectors configured to monitor the operating temperature of the dual carbon monoxide-methane sensor and/or the oxygen sensor.

In this embodiment, sampling pipe 104 is configured to extend within a flue, such as flue 14. Probe 104 includes a proximal end 118 that is adjacent to flange 120. Flange 120 is used to mount or otherwise secure the transmitter 100 to the sidewall of the flue. When so mounted, analyzer 100 can be completely supported by the coupling of flange 120 to the flue wall.

Electronics 106 provide heater control and signal conditioning, resulting in a mA signal representing flue gas oxygen concentration. Preferably, electronics 106 also includes a controller/microprocessor that is able to execute programmatic steps. Electronics 106 can also include a variety of other components including, but not limited to, measurement circuitry (e.g. a measurement cell), communication circuitry (e.g. a transmitter), power source(s), resistance temperature detector(s) (RTD), temperature sensors and any other suitable electrical components. Electronics 106 can also include a local operator interface 134 configured to display information (e.g. gas concentration measurements) and to allow for operator interaction. Interface 134 can include a number of interaction features, for example, lockout features, a touch screen, status indicators, selection keys (e.g. for interaction with a menu), and any other suitable features.

In one example, combustion analyzer 100 can be implemented with commercially available combustion analyzers, for example, a Model OCX 8800 combustion analyzer available from Rosemount Inc., of Shakopee, Minn. (an Emerson company). The OCX 8800 combustion analyzer is an extractive analyzer and, similar to an in-situ oxygen probe, is installed on a combustor duct wall. The analyzer is driven by an eductor with compressed air, creating suction of process fluid (e.g. flue gases) via the Venturi effect. Flue gas is pulled through the sampling pipe with external and internal filters and delivered to the oxygen sensor and the dual carbon monoxide-methane sensor, whereby concentrations of the gases of interest can be measured.

Figure 3:
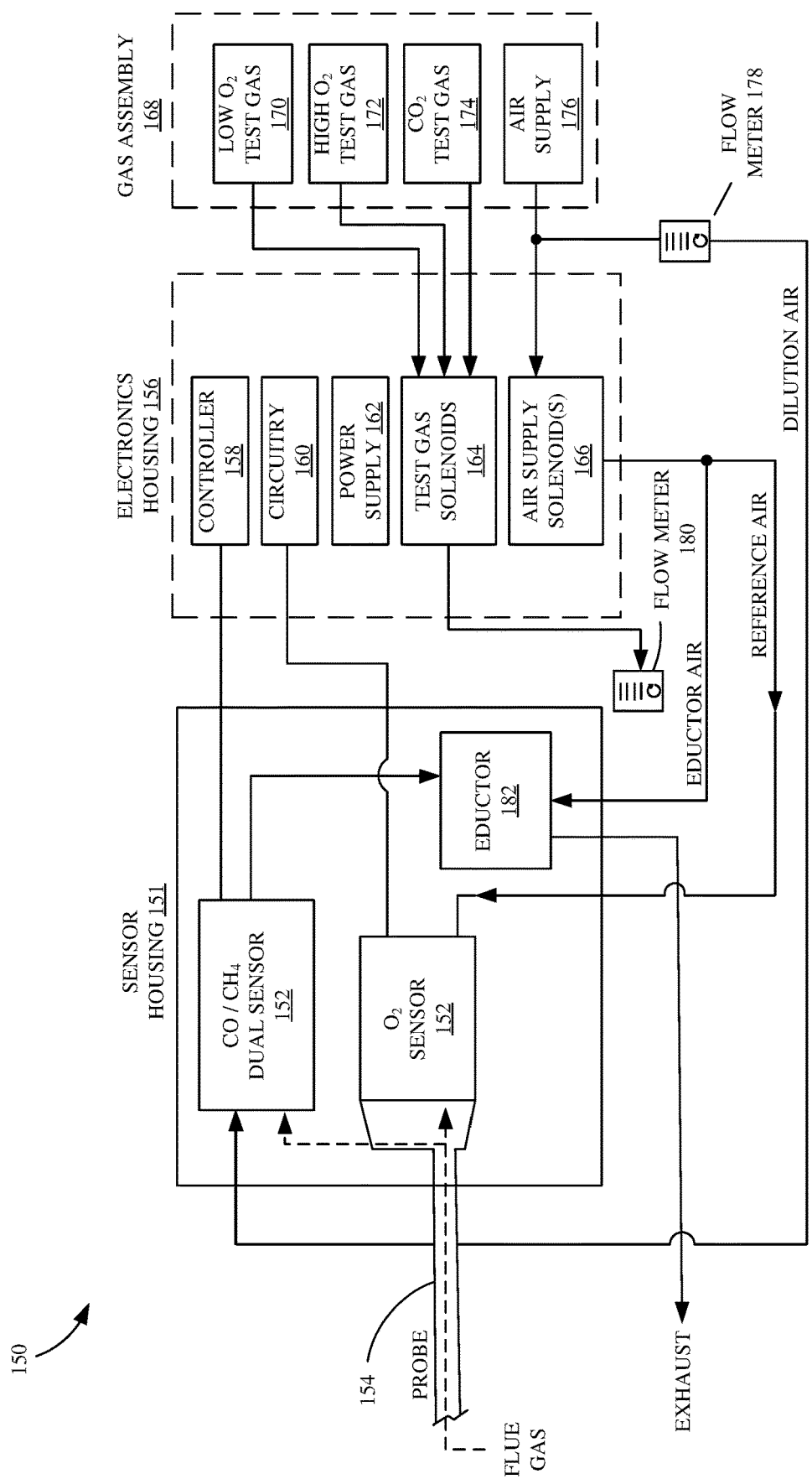
FIG. 3 is a simplified block diagram showing one example of a combustion analyzer.

FIG. 3 is a simplified block diagram showing one example of a combustion analyzer. Combustion analyzer 150 includes sensor housing 151. Within sensor housing 151 are sensors 152, shown as an oxygen sensor and a dual carbon monoxide-methane sensor. Sensors 152 are similar to those described herein (e.g. 112). Also within sensor housing 151 is an eductor 182. Analyzer 150 further includes electronics housing 156. Within electronics housing 156 are controller(s) 158, which can comprise microprocessor(s), circuitry 160, which can comprise measurement circuitry (e.g. a measurement cell) and/or communication circuitry (e.g. a transmitter), and power supply 162. Also, within electronics housing 156 are test gas solenoids 164 and air supply solenoid(s) 166.

Analyzer 150 further includes gas assembly 168. Gas assembly 168 includes low oxygen test gas source 170, high oxygen test gas source 172, carbon monoxide test gas source 174 and air supply source 176. The sources are configured to provide the flow of gases to analyzer 150 for the purpose of measurement, calibration and other functionalities. In other examples, analyzer 150 may include additional test gas sources and/or the combination of the above listed gas sources may be configured to provide the flow of other test gases, including methane test gas sources configured to provide the flow of methane to components of analyzer 150 (e.g. sensors 152) for the purposes of calibration and other functionalities. Analyzer 150 further includes air supply flowmeter 178 and test gas flowmeter 180. The flowmeters are configured to monitor and control the flow of air and test gases to components of analyzer 150. Analyzer 150 also includes sampling tube 154 which is configured (e.g. via an aperture disposed at a distal end) to allow the flow of flue gases to sensors 152 such that gas concentration measurements can be taken by analyzer 150.

Analyzer 150 is mounted to a duct or flue/stack wall such that sampling tube 154 is exposed to the process flow. Eductor 182, which is air powered via a compressor and air supplied via air supply 176, continuously pulls samples of the process flue gas through the probe to a chamber in front of the sensor housing where the sample passes through sensors 152. The sample is then drawn through eductor 182 where it mixes with the eductor air and exits through exhaust and back into the process. Controller 158 and circuitry 160 receive, analyze and convert the generated sensor signals from sensors 152 into digital output signals indicative of a concentration of gases within the sample. Controller 158 can, based on the concentrations of gases detected by sensors 152 for example, initiate calibration operations, shutdown operations, adjust the flow of air and gas to the combustion process, generate alerts/alarms, surface displays indicative of the measured concentrations, and various other operations. Test gases 170, 172 and 174 can be turned on and off by solenoids 164, based on control signals from controller 158. Test gas flow to sensors 152 is regulated by test gas flow meter 180. In one example, flowmeter 180 is disposed between housings 151 and 156. Air supply 176 can be turned on and off by air supply solenoid(s) 166, based on control signals from controller 158. In one example, air supply 176 is not turned on until sensors 152 are at the desired operating temperatures (e.g. heated to the desired temp by a heater). This minimizes the amount of sampled process flue gas being pulled into cold sensors which causes condensation. Air supply 176 is separated into educator air, reference air, and dilution air. Dilution air is provided to sensors 152 to ensure that there is adequate oxygen to fully oxidize any combustible gases regardless of the concentration of oxygen in the process.

Combustion analyzers 10, 100 and 150 measure oxygen, carbon-monoxide and/or methane simultaneously. The low burning velocity of methane in a calorimetric catalytic carbon monoxide sensor (e.g. sensors 112) can be enhanced by operating the sensor at a higher temperature. A standard calorimetric catalytic carbon monoxide sensor employed in a combustion analyzer is typically operated at 300° C. This temperature is optimized for carbon monoxide sensitivity with no cross-sensitivity to methane and produces reliable and repeatable measurement of carbon monoxide but fails to provide for measurements of methane. In one example, the combustion analyzer (e.g. 10, 100, and/or 150) increases the temperature of the dual carbon monoxide-methane sensor (e.g. sensors 112) via a controller (described below). In one example, the temperature is increased to 400° C. In another example, the temperature is increased to 600° C. In yet another example, the temperature is increased to a temperature falling in the range of 400-600° C. In another example, the oxygen sensor is operated at a temperature of 700° F. In another example, the oxygen sensor is operated at a temperature above 700° F.

Increasing the sensor temperature permits partial methane oxidation on the catalyst surface, thereby allowing for the measurement of both carbon monoxide and methane simultaneously. Generally, the released heat in the reaction (e.g. methane/carbon monoxide oxidation on the catalyst surface) is measured by a resistance temperature detector (RTD) employed in the electronics of the combustion analyzer.

While increasing the temperature of the dual sensor allows for the measurement of methane concentrations, it slightly reduces the combustion analyzer's sensitivity to carbon monoxide. This happens because of ongoing carbon monoxide combustion at the higher temperatures outside of the catalytic surface (e.g. on the stainless-steel sensor block) and heat losses through radiation.

Combustion analyzers 10, 100 and 150 can all also include one or more heaters and/or other heat supply components configured to provide and/or otherwise assist in the regulation and control of their various sensors operating temperature (e.g. by heating up or reducing the heat of the sensor block). In one example, heaters and/or other heat supply components can, based on a control signal for example, adjust the operating temperature of the sensors. In one example, combustion analyzers 10, 100 and 150 can include a heater strut assembly, including, but not limited to, wiring, thermal switches, heater rods, insulators, heater clamps, thermocouples and any other suitable components and/or devices. In another example, analyzers 10, 100 and 150 can include a band heater. In another example, analyzers 10, 100 and 150 can include a ceramic fiber heater. In another example, analyzer 10, 100 and 150 can include any other suitable device(s) and/or components suitable to maintain and regulate the operating temperature of the various sensors and/or other devices and/or components of analyzers 10, 100 and 150.

Figure 4:
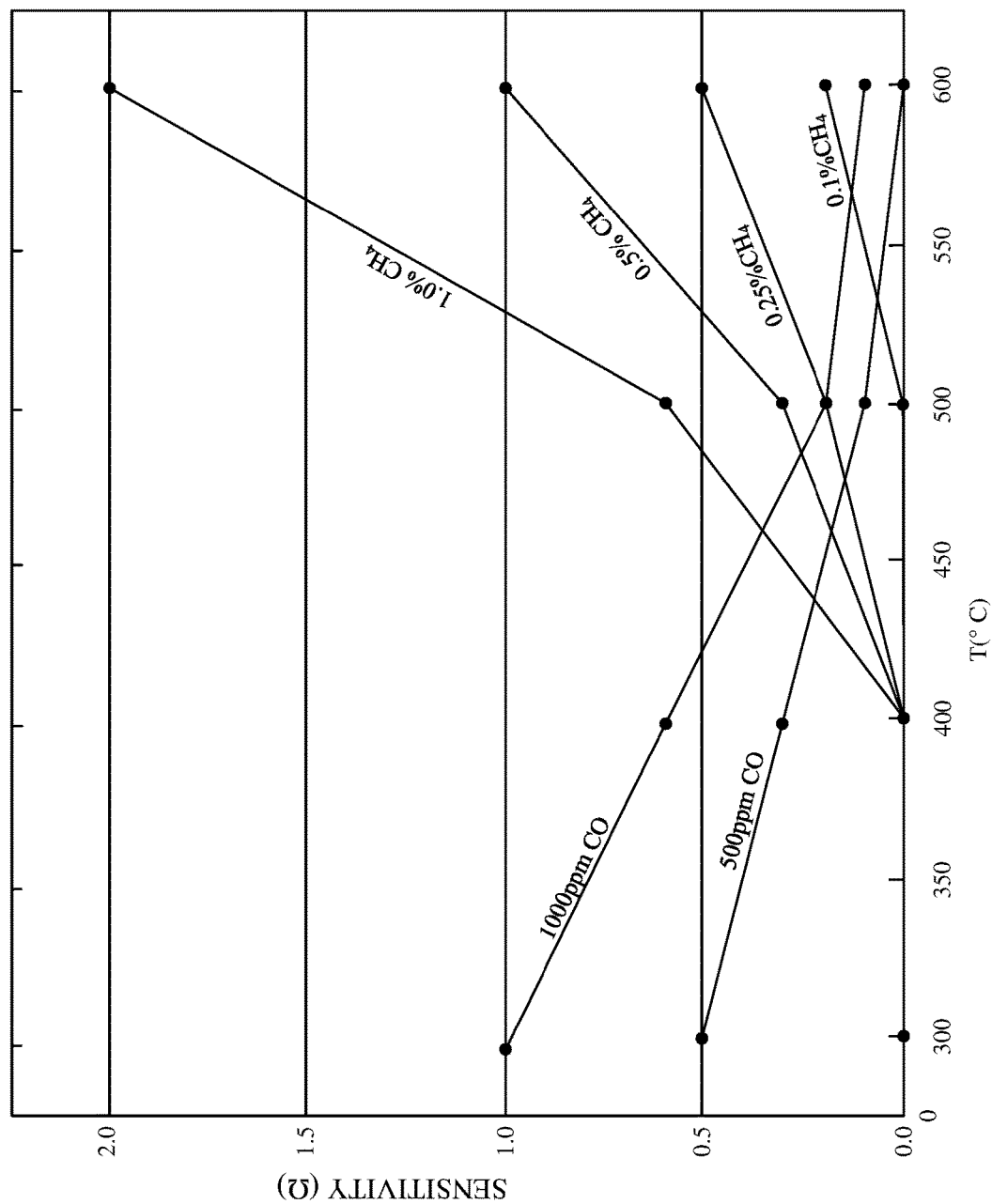
FIG. 4 is a graphical representation of the effect of temperature on a dual calorimetric carbon monoxide and methane sensor's sensitivity

FIG. 4 is a graphical representation of the effect of temperature on a dual calorimetric carbon monoxide and methane sensor's sensitivity. Generally, FIG. 4 shows that as the temperature of the dual sensor increases, the sensitivity to carbon monoxide decreases and the sensitivity to methane increases. As can be seen, at 300° C., the dual sensor is optimized for carbon monoxide detection, as the sensitivity (as measured in Ohms) reading is approximately representative of the actual concentration of carbon monoxide. As the temperature increases to 400° C., the dual sensor becomes measurably sensitive to methane but is less sensitive to carbon monoxide. As is shown in FIG. 4, as the temperature of the dual sensor continues to increase towards 600° C. the sensitivity to methane increases, allowing for more selective methane percentage detection (e.g. 1.0%, 0.5%, 0.25%, 0.1% as shown in the FIG. 4). The sensitivity to carbon monoxide continues to decrease, however, readable measurements of carbon monoxide are still available at 600° C. where the sensitivity to methane is optimized.

However, the combustion analyzer is still able to reliably and reproducibly measure carbon monoxide, and any error can be accounted for through methods of calibration, as will be described below.

Figure 5:
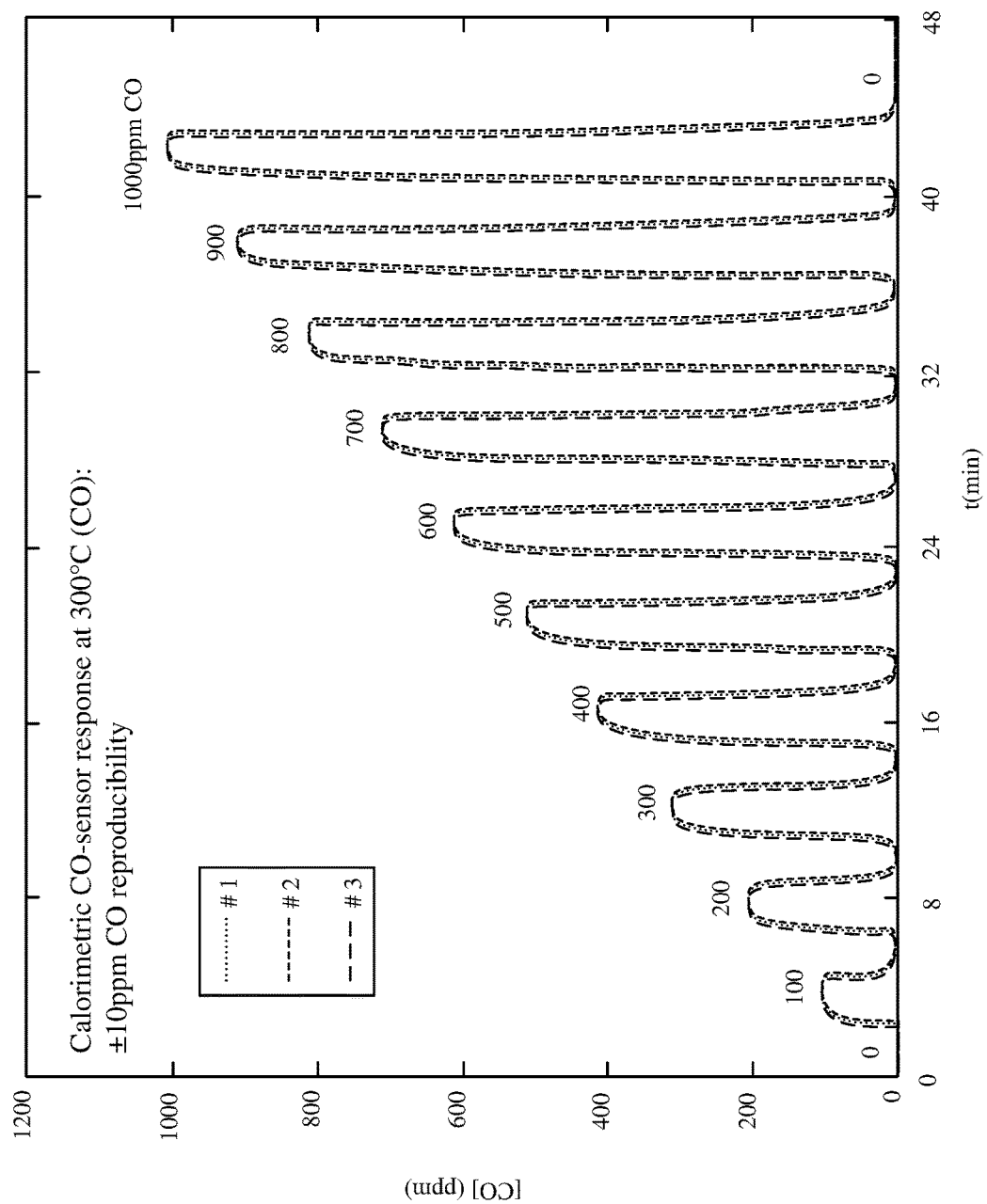
FIGS. 5-7 are graphical representations of gas concentration measurements using a combustion analyzer.
Figure 6:
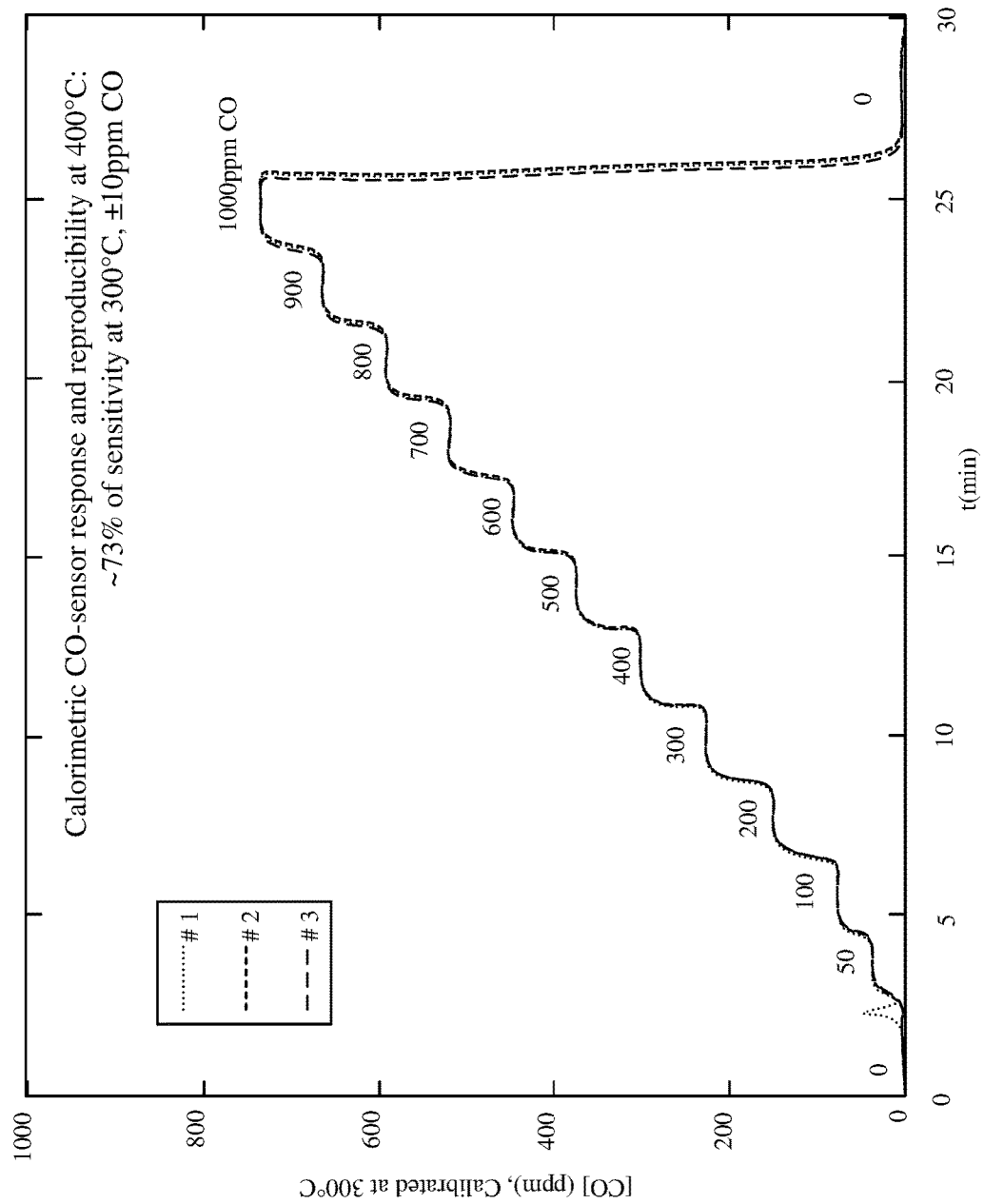
Figure 7:
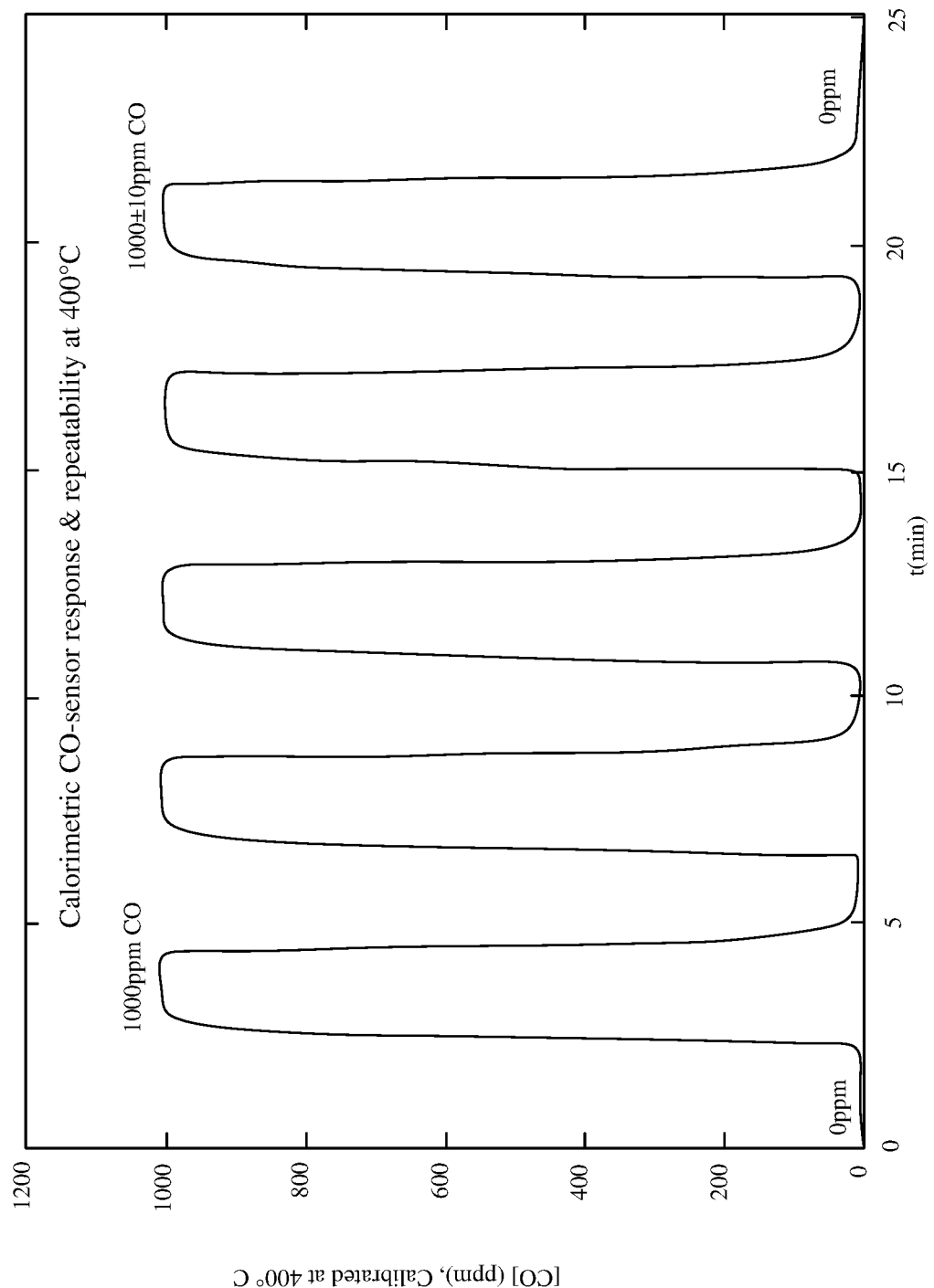

FIGS. 5-7 are graphical representations of gas concentration measurements using a combustion analyzer. FIG. 5 shows carbon monoxide measurements of a combustion analyzer in accordance with the prior art. Specifically, FIG. 5 illustrates the response of a catalytic carbon monoxide sensor operated at 300° C., specifically illustrating a catalytic carbon monoxide sensor's step response for a carbon monoxide range of 0-1000 ppm. As mentioned previously, a standard calorimetric catalytic carbon monoxide operated at 300° C. produces reliable measurement of carbon monoxide. As can be seen in FIG. 5, the sensor is approximately 100% responsive (plus or minus 10 ppm). In other words, when the process environment contains a carbon monoxide concentration of a certain ppm (e.g. 1000 ppm) the sensor is producing a reading that is corresponding to the actual concentration (plus or minus 10 ppm). However, at this operating temperature, the sensor is not able to detect the presence of or measure the concentration of methane.

FIG. 6 shows carbon monoxide measurements of a combustion analyzer. Specifically, FIG. 6 illustrates what happens to a catalytic carbon monoxide sensor's sensitivity when the sensor is heated to 400° C., but is calibrated for 300° C. As mentioned above, increasing the temperature of the sensor allows for the detection and measurement of methane. However, the increase in temperature also reduces the sensitivity to carbon monoxide. As can be seen, the sensor's reading is approximately 73% of the actual carbon monoxide value. For example, at a carbon monoxide concentration of 1000 ppm, the sensor reading is approximately 730 ppm. While the reduced sensitivity is undesirable, it can be corrected through a calibration operation as will be shown in FIG. 7 and discussed in further detail below.

FIG. 7 shows carbon monoxide measurements of a combustion analyzer in accordance with an example of the present invention. Specifically, FIG. 7 shows the sensor readings of a catalytic carbon monoxide sensor that has been heated to and calibrated for 400° C. As can been in FIG. 7, the readings of the sensor correspond to the actual concentration of carbon monoxide, plus or minus 10 ppm, and these readings are reliable and reproducible. For example, after calibration for 400° C., when the concentration of carbon monoxide is at 1000 ppm, the sensor readings come back at approximately 1000 ppm, and do so repeatedly and consistently.

Figure 8:
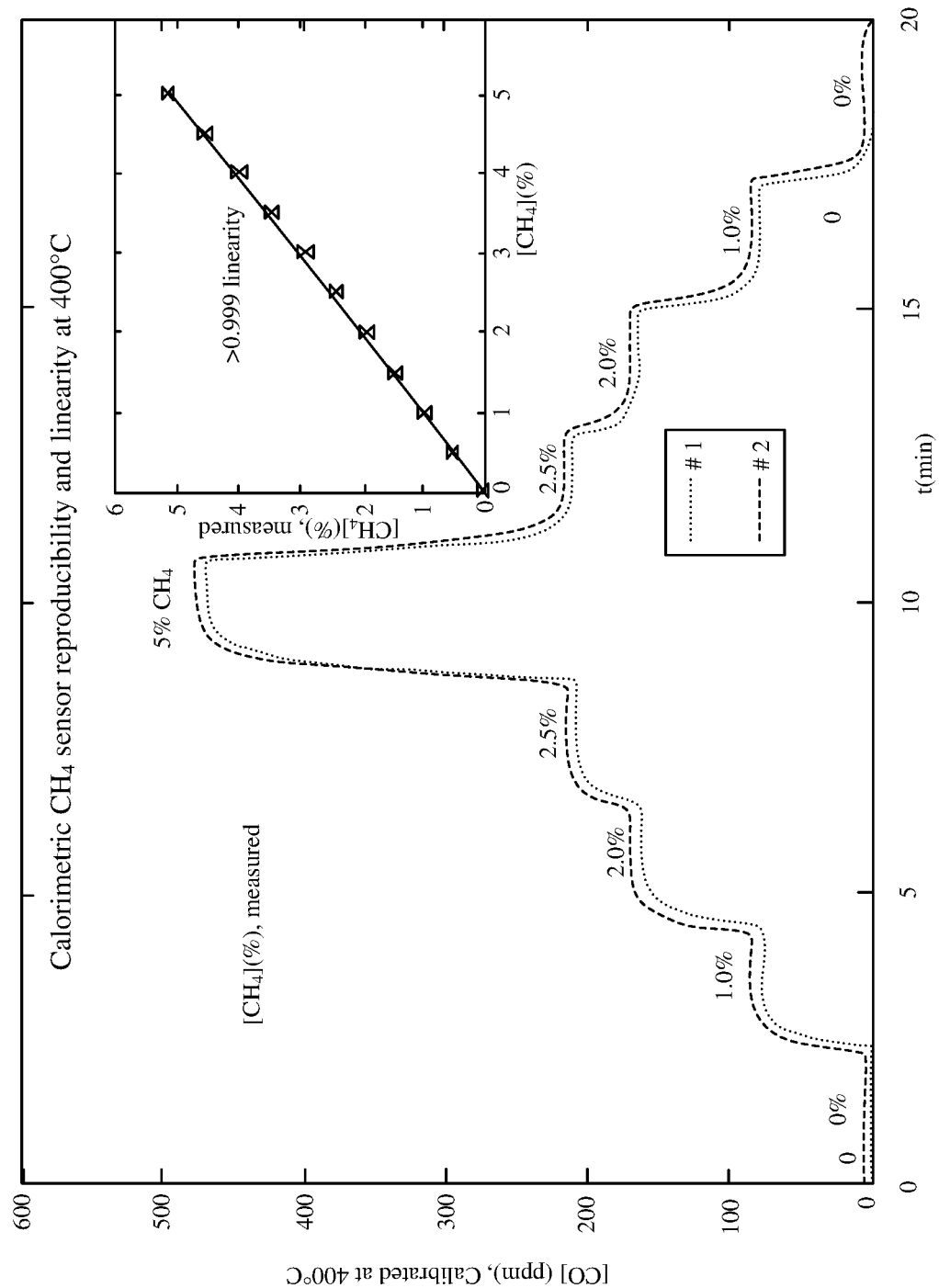
FIGS. 8-10 are graphical representations of gas concentration measurements using a combustion analyzer in accordance with an example of the present invention.
Figure 9:
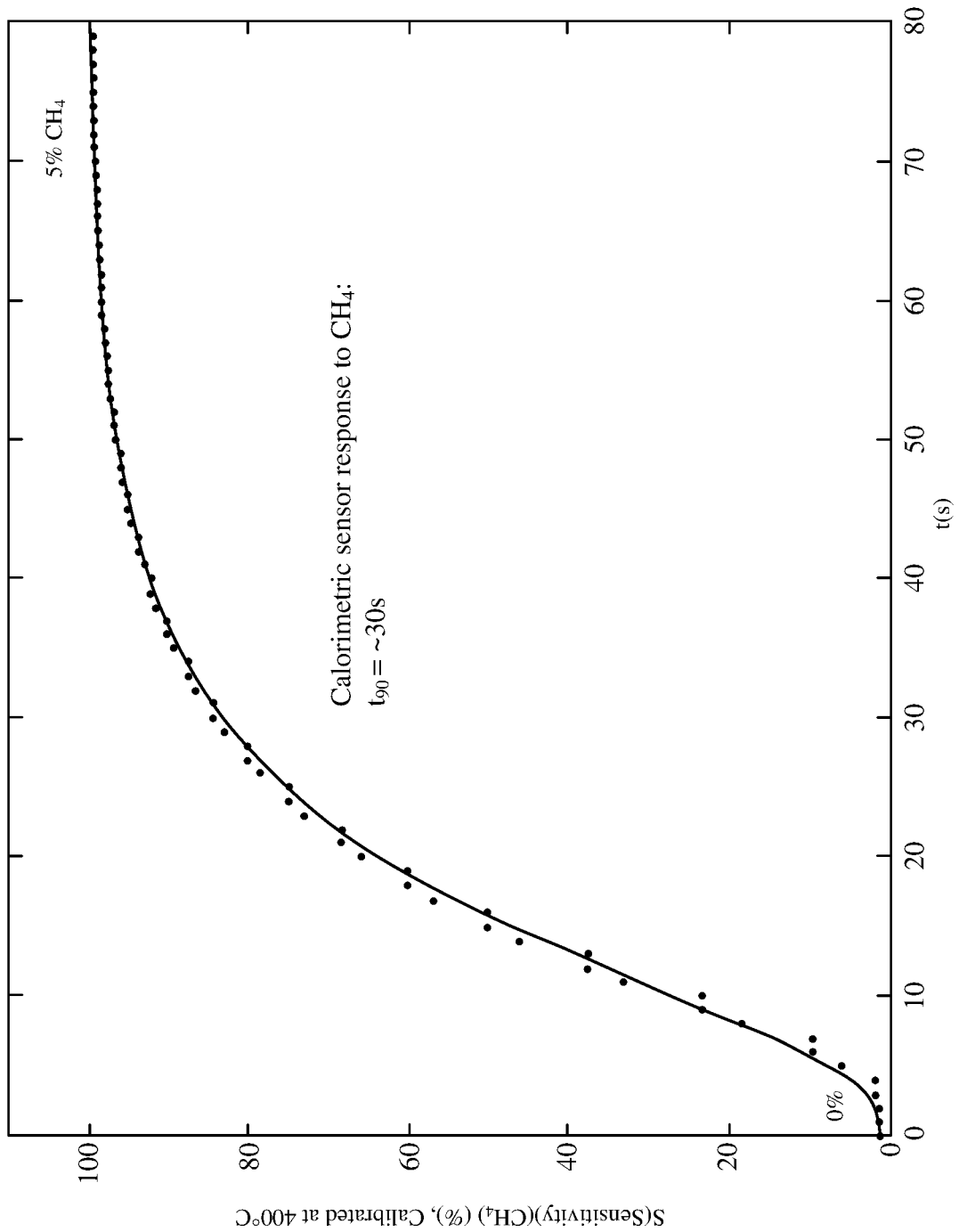
Figure 10:
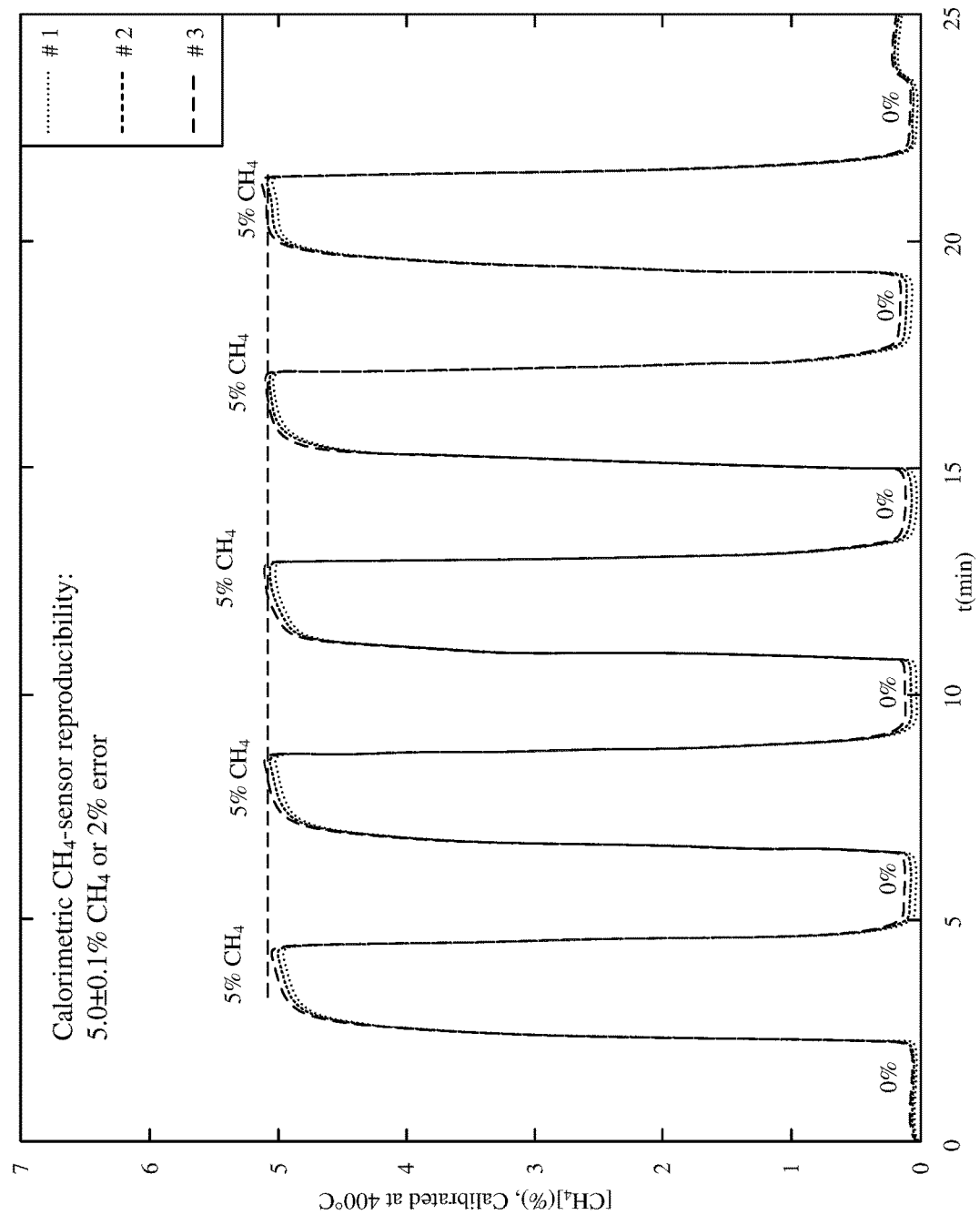

FIGS. 8-10 are graphical representations of gas concentration measurements using a combustion analyzer in accordance with an example of the present invention. Specifically, FIGS. 8-10 show the readings of a dual calorimetric carbon monoxide-methane sensor. As previously mentioned, by heating the sensor to and calibrating for 400° C., the sensor is able to detect the presence and measure the concentration of methane. The sensor response is reliable and reproducible, as can be seen in FIGS. 8-10.

FIG. 8 shows methane measurements of a combustion analyzer in accordance with an example of the present invention. Specifically, FIG. 8 shows the methane concentration measurements of a dual calorimetric carbon monoxide-methane sensor heated to and calibrated for 400° C. As can be seen in FIG. 8, the sensor response spans from 0 to up to 5.0% methane concentration expressed in ppm carbon monoxide. The sensor response also shows good linearity (graph in top right of FIG. 8), thus only requiring a two-point calibration, and spans approximately 5.0%, resulting in a reliable approximately plus or minus 0.2-0.3% methane detection option. A two-point calibration is possible in cases where the sensor output is known to be reasonably linear (i.e. the change in x-axis value is proportional to the change in y-axis value and/or where the output is directly proportional to the input). Linearity eliminates the need to do any complex curve-fitting (e.g. a regression analysis) and only requires two points of reference to map a line. A two-point calibration essentially re-scales the output and is capable of correcting both slope and offset errors. One example of a two-point calibration equation is as follows:

Corrected Value=(((RawValue−RawLow)×Reference Range)÷RawRange)+ReferenceLow     Equation 2

FIG. 9 shows methane measurements of a combustion analyzer in accordance with an example of the present invention. Specifically, FIG. 9 shows the response of the dual calorimetric carbon monoxide-methane sensor. As can be seen in FIG. 9, the sensor, at temperatures of 400° C., methane oxidation on the catalyst surface is detectable with a response time in the range of 30 seconds for a 90% response, allowing for reliable and efficient methane detection for safe combustion control.

FIG. 10 shows methane measurements of a combustion analyzer in accordance with an example of the present invention. Specifically, FIG. 10 shows the reproducibility of the response of the dual calorimetric carbon monoxide-methane sensor heated to 400° C. As can be seen in FIG. 10, the sensor readings correspond to the actual concentration of methane, e.g. 5.0% plus or minus 0.1 percent, and do so reliably and reproducibly, being exposed to a methane range of 0-5.0% over the course of time.

Figure 11:
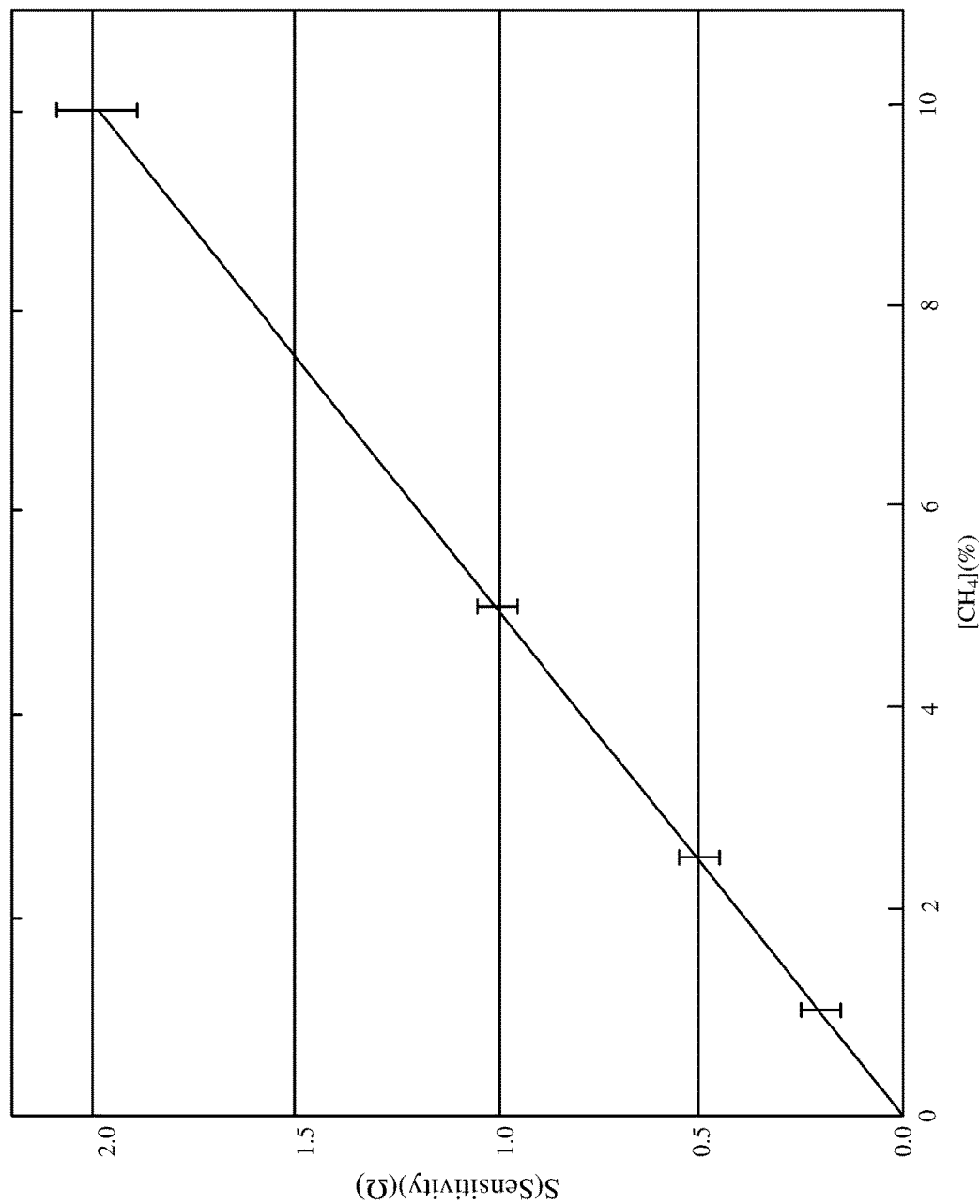
FIG. 11 is a graphical representation showing methane measurements of a combustion analyzer in accordance with an example of the present invention.

FIG. 11 is a graphical representation showing methane measurements of a combustion analyzer in accordance with an example of the present invention. As can be seen in FIG. 11, the measurements from the dual carbon monoxide-methane sensor as to methane, when the dual sensor is heated to 600° C., are linear. As the concentration of methane increases, the reading (in Ohms) increases proportionally. The linearity allows for a two-point calibration of the sensor.

Figure 12:
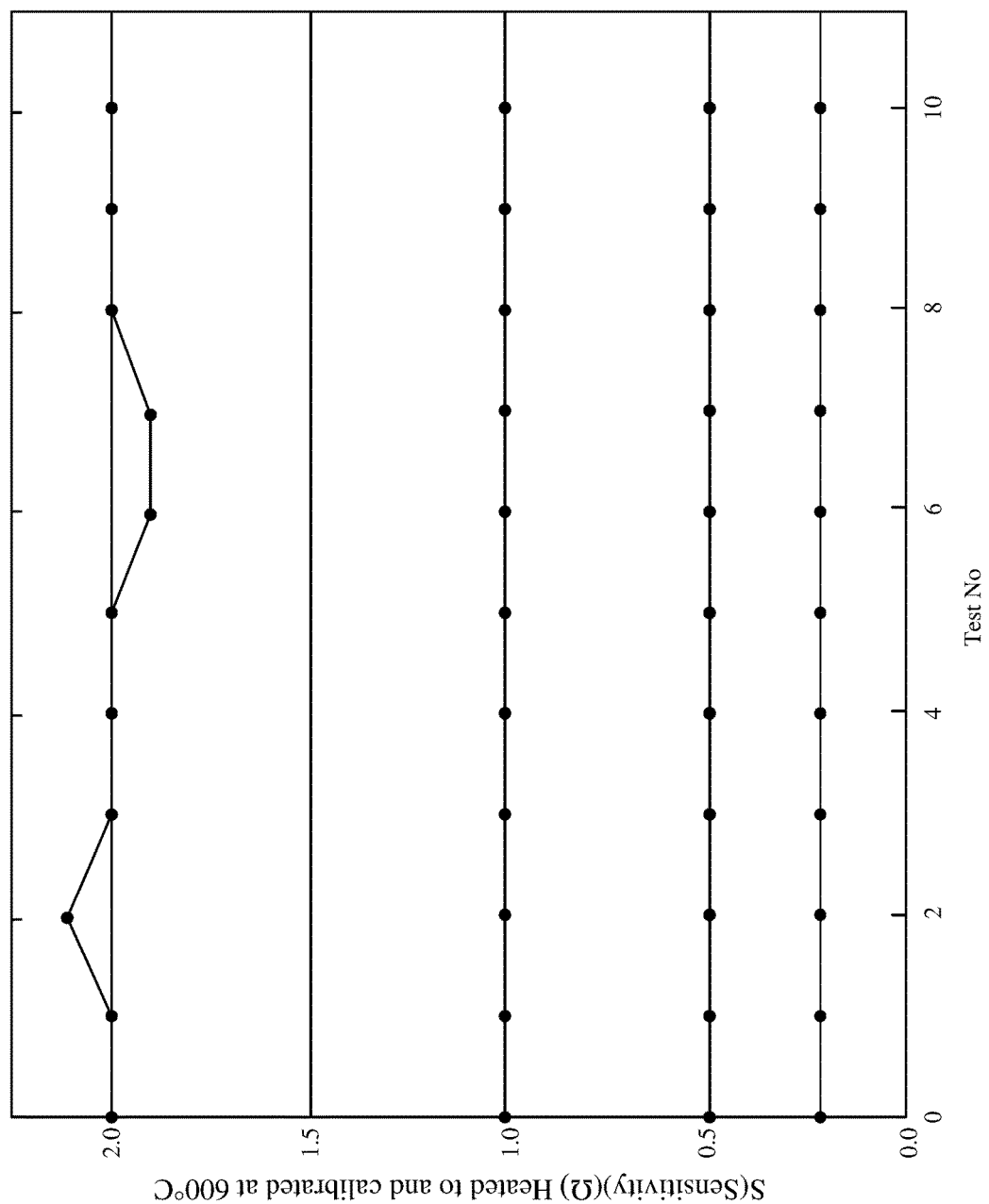
FIG. 12 is a graphical representation showing methane measurements of a combustion analyzer in accordance with an example of the present invention.

FIG. 12 is a graphical representation showing methane measurements of a combustion analyzer in accordance with an example of the present invention. As can be seen in FIG. 12, using a dual carbon monoxide-methane sensor heated to 600° C. over a series of tests at different concentrations of methane, the dual sensor measurements have good repeatability and are reproducible.

During combustion, there are two primary operational scenarios. The first is when the fuel is ignited at start-up. The operator trims the oxygen level down toward the stoichiometric point and carbon monoxide is measured and controlled for safety and to help improve efficiency (i.e. efficient mixture of air and fuel). The second operational scenario occurs when ignition does not occur at start-up and the oxygen level remains high. Methane is measured, and if the levels remain high it indicates that ignition did not happen. In order to detect the presence of methane, the calibration algorithm (as shown in FIGS. 5-12 and described below) is employed in the electronics of the combustion analyzer (e.g. a processor/controller), thereby either heating the sensor to 400° C., and calibrating the sensor to correct the readings, or, if the sensor is already at 400° C., correcting the readings to measure the concentration of methane. In one example, the combustion analyzer methane sensor detects that methane is present and a controller (described below) can trigger an alert or alarm to notify the operator, thereby alerting the operator to the presence of methane and the likelihood that ignition did not occur.

The combustion analyzer is calibrated with carbon monoxide, for example 1000 ppm and methane, for example 5.0% (as shown in FIGS. 5-10). This calibration can be done using a calibration gas assembly (e.g. 28), which allows calibration gases (with known concentrations) to be exposed to the combustion analyzer. The combustion analyzer detects the presence of the calibration gases and generates a signal indicative of a concentration of those gases. Any error in the concentration detected by the analyzer can be corrected for, using, for example, a two-point calibration method (wherein a reference measurement can also be used, for example, with a reference sensor having a known accurate response); particularly when the error is reproducible and reliable, and the sensor response shows good linearity (as shown in FIGS. 5-12). This calibration operation allows for reliable ppm carbon monoxide range and methane percentage detection.

In one example, the sensor is then operated at the elevated temperature of 400° C. In another example, the sensor is operated at the elevated temperature of 600° C. In yet another example, the sensor is operated at a temperature in the range of 400° C.-600° C. When the combustion analyzer detects oxygen measurements of less than 10.0%, the carbon monoxide calibration algorithm is employed to detect a percentage of carbon monoxide. When the combustion analyzer detects oxygen measurements greater than 20.0%, the methane calibration algorithm is employed to detect a percentage of methane. The combustion analyzer, in some examples, will send an alert or an alarm upon a detection of greater than 1.0% concentration of methane. An operator will then stop fuel flow and avoid dangerous ignition and explosion scenarios. In some examples, upon a detection of greater than 1.0% concentration of methane, the combustion analyzer will automatically stop fuel flow, for example, by sending a control signal to shut off the flow of fuel or air (e.g. as mentioned in FIG. 1). In other examples, the concentration threshold can be different from those described above. In another example, the concentration threshold is user selectable.

Figure 13:
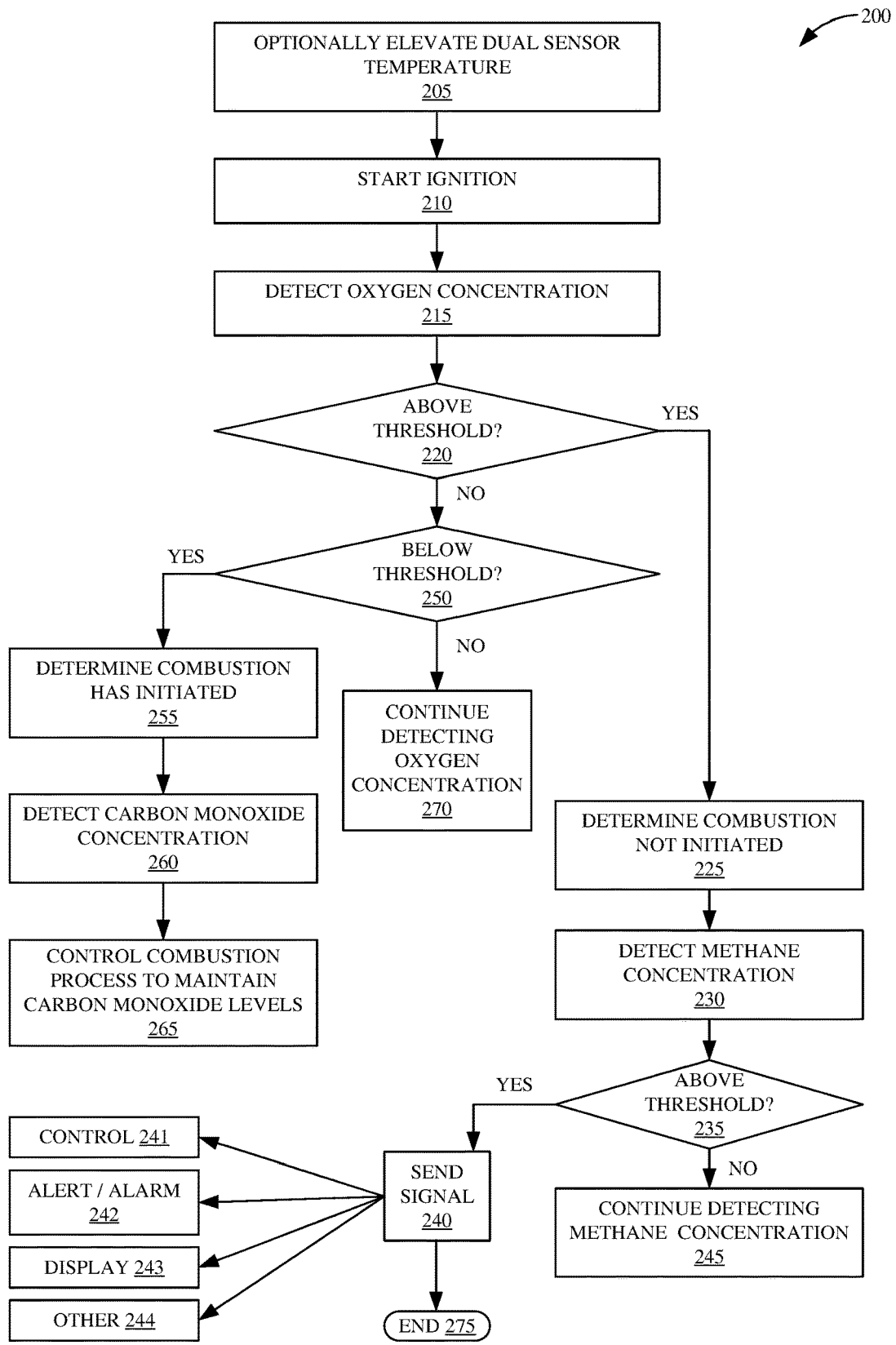
FIG. 13 is a flowchart showing one example of a method for the monitor and control of a combustion process.

FIG. 13 is a flowchart showing one example of a method for the monitor and control of a combustion process. Method 200 begins at block 205 where a combustion analyzer capable of simultaneously measuring oxygen, carbon monoxide, and methane concentrations, such as the combustion analyzer discussed herein (e.g. 10 and 100), is placed in the combustion process flow and the dual calorimetric carbon monoxide-methane sensor is optionally set to an elevated temperature. In one example, the elevated temperature is 400° C. In another example, the elevated temperature is 600° C. In another example, the elevated temperature falls within a range of 400-600° C. It is not necessary to elevate the temperature of the dual temperature sensor at the beginning of this process. In one example, the temperature will only be elevated upon detection of a concentration of oxygen at or above a certain threshold, as will be discussed further below. In one example, the temperature remains at 300° C. at the beginning of the process, and thus the analyzer is optimized for carbon monoxide detection.

Method 200 continues at block 210 where the combustion process begins, and the ignition sequence is initiated.

Method 200 continues at block 215 where the combustion analyzer determines the concentration of oxygen in the combustion process. The detection of the oxygen concentration at block 210, can, for example, be done with an oxygen sensor within and electrically coupled to components of the combustion analyzer, that senses the presence of oxygen in the combustion flow and generates a sensor signal (e.g. a millivolt signal). The sensor signal is then fed to measurement circuitry, electrically coupled to the sensor, where one or more characteristics of the sensor signal is measured (e.g. varying electrical characteristics of the sensor signal) and data is then provided to a controller (e.g. microprocessor(s)) indicative of a concentration of oxygen.

Method 200 continues at block 220 where the combustion analyzer determines whether the concentration of oxygen is at or above a certain threshold. In one example, the threshold is 20.0% oxygen. In another example, the threshold is 20.9% oxygen. If the oxygen concentration at block 220 is above the threshold, method 200 continues at block 225 where the combustion analyzer determines that combustion has not been initiated (i.e. ignition did not occur). As mentioned above, failure to ignite can lead to a hazardous situation, causing a build up of explosive/flammable mixture (e.g. air and fuel).

In order to prevent this hazardous situation, method 200 continues at block 230 where the combustion analyzer detects the methane concentration in the combustion process flow. The detection of methane, occurs, in one example, by applying the methane calibration algorithm described in FIGS. 8-12. Optionally, at block 230, the dual carbon monoxide-methane sensor is heated to an elevated temperature (if it was not done previously at block 205). The elevated temperature can be, for example, 400° C., 600° C., or in the range of 400° C.-600° C. Method 200 continues at block 235 where the combustion analyzer determines whether the methane concentration is above a threshold. In one example, the threshold is 1.0% methane concentration. In another example, the threshold is 5.0% methane concentration. In another example, the threshold falls in a range of 1.0-5.0% methane concentration.

If at block 235, the methane concentration is determined to be above the threshold, method 200 continues at block 240 where the combustion analyzer sends a signal. In one example, the signal is a control signal 241 configured to automatically stop the combustion process and prevent ignition by stopping the flow of fuel and air (e.g. by shutting valves 24 & 26) and/or shutting down the installation. In another example, the combustion analyzer sends an alert and/or alarm signal 242 that visually or audibly indicates that the combustion process should be shut down and that there is a hazardous situation. In one example, the alert/alarm can be a visual alert/alarm, such as, but not limited to, lights electrically or communicatively coupled to the combustion analyzer. In another example, the alert/alarm can be an audible alert/alarm, such as, but not limited to, a device that emits noise (e.g. a horn or siren) electrically or communicatively coupled to the combustion analyzer. The signal can be display signal 243 configured to surface an indication on a user interface. The user interface could be a local interface coupled to the analyzer or installation, a handheld device, or a remote device such as a computer in a control room. The signal could be any other kind of signal 244 configured to indicate a status of the combustion installation, for example, but not limited to, text message alerts, emails, a phone call, or any other suitable techniques. Method 200 ends at block 275 where the combustion process is shut down and reignition will not occur until safe concentrations of gases/fuel in the combustion process flow are detected.

If at block 235, the methane concentration is determined to not be above the threshold, method 200 continues at block 245 where the combustion analyzer continues to detect the concentration of methane.

Returning to block 220, if it is determined that the oxygen concentration is not above the threshold, method 200 continues at block 250 where it is determined if the oxygen concentration is below a threshold. In one example, the threshold is 10.0% oxygen concentration. If, at block 250, it is determined that the oxygen concentration is below the threshold, method 200 continues at block 255 where the combustion analyzer determines that combustion has been initiated (e.g. ignition has occurred). Method 200 continues at block 260 where the combustion analyzer detects the concentration of carbon monoxide in the combustion process flow. In one example, detection occurs by applying the carbon monoxide calibration algorithm described in FIGS. 5-7. Optionally, at block 260, the dual carbon monoxide-methane sensor's temperature is reduced, if, for example, the temperature was elevated at block 205. In one example, the dual sensor's temperature is set to 300° C. In another example, the dual sensor's temperature falls within a range of 400-600° C.

The method continues at block 265 where the combustion analyzer controls the combustion process to maintain concentrations of carbon monoxide. In one example the concentration is 100 ppm. In another example, the concentration is 200 ppm. In another example, the concentration falls between 100-200 ppm. The combustion analyzer continues to control the combustion process to maintain concentrations of carbon monoxide until the combustion process ends (e.g. shut down).

Returning to block 220, if the concentration of oxygen is determined by the combustion analyzer to not be above the threshold and determined to not be below the threshold at block 250, the method continues at block 270 where the combustion analyzer continues detecting the concentration of oxygen.

It should be noted that while method 200 was described, for illustrative purposes and for the sake of explanatory clarity, in a certain order, those skilled in the art will understand that the steps of method 200 can be completed in varying orders and that no specific order was intended by this illustration.

Figure 14:
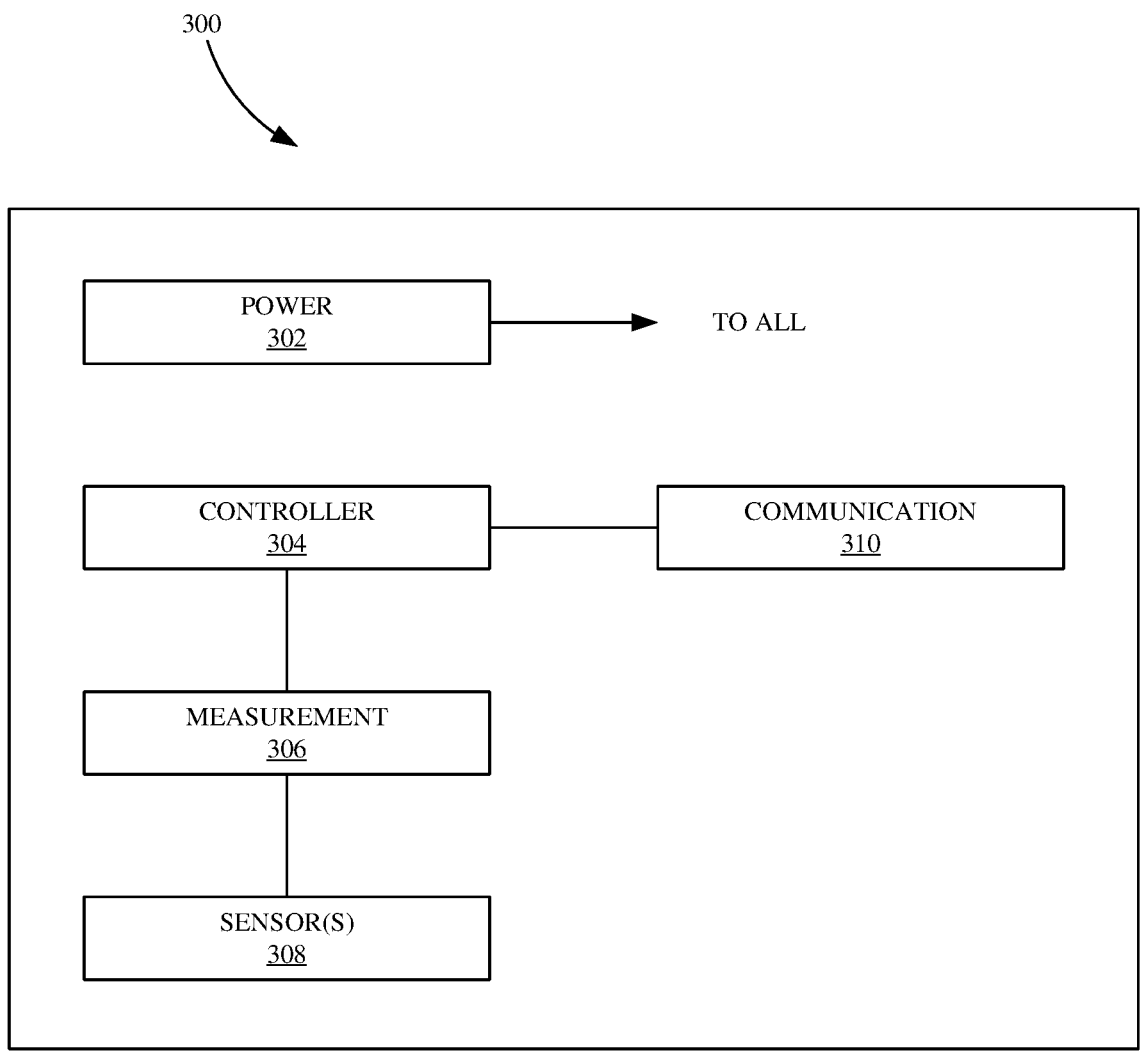
FIG. 14 is a simplified block diagram showing one example of a combustion analyzer.

FIG. 14 is a simplified block diagram showing one example of a combustion analyzer. Combustion analyzer 300 includes power source 302, controller 304, measurement circuitry 306, sensor(s) 308, communication circuitry 310, and other 312. Power source 302 is configured to provide power to combustion analyzer and the components thereof (as shown by the arrow "to all"). Power source 302 can be a local power source, such as, but not limited to, a replaceable battery or a rechargeable battery. Power source 302 can be an external power source, for example an electrical circuit wherein power source 302 comprises a power cord (or other wiring) that plugs in (or otherwise connects) to the electrical circuit via, for example, an outlet. Sensor(s) 308 can include a variety of sensors, including sensors that are configured to detect the presence of gases in a combustion process and generate signal(s) indicative of the concentration of those gases and/or temperature sensors (e.g. a resistance temperature detector) configured to monitor the temperature of the sensors (e.g. the operating temperature of the dual carbon monoxide-methane sensor). Sensor(s) 308 can comprise an oxygen sensor and dual carbon monoxide-methane sensor (as mentioned above, e.g. sensor(s) 112). Sensor(s) 308 can also comprise electrochemical oxygen sensor based on zirconia solid electrolyte and a dual carbon monoxide-methane calorimetric catalytic sensor configured to simultaneously measure carbon monoxide and/or methane.

The sensor signal(s) from sensor(s) 308 are sent to measurement circuitry 306 where the concentration of gases present in the combustion process, sensed by sensor(s) 208, is measured based on the signal(s). Controller 304 can then generate a variety of control signals based on the measured concentration. In one example, the control signal can be configured to trigger an alarm an alarm or alert. In another example, the control signal can be configured to adjust the flow of air and fuel to the combustion process, for example, by adjusting a valve (e.g. opening or closing) as mentioned above in FIG. 1. In another example, the control signal can be configured to shut-off the combustion process. In another example, the control signal can be configured to adjust (e.g. elevate or decrease) the operating temperature of the sensor(s) 308. The temperature, in one example could fall within a range of 300-600° C.

In another example, the control signal can be configured to send an output to display the detected gases and determined concentrations, via communication circuitry 310. The output can be displayed on a number of user interfaces including lights, a display screen, a handheld device, or a remote interface, for example a computer in a control room. Communication circuitry 310 can be configured to communicate wirelessly, for example via connectivity to a wireless network or Bluetooth protocol. Communication circuitry 310 can be configured to communicate via a wired loop connected to the corresponding user interface or other visual/audible devices (e.g. flashing lights, horn or siren). Communication circuitry 310 can comprise a transmitter. Communication circuitry 310 can be configured to allow for the communication of components of the combustion analyzer to communicate with one another. Communication circuitry 310 can be configured to allow external communication to be communicated to components of the combustion analyzer (e.g. communication from an operator or a control system, for example, a computer in a control room). Communication circuitry can be configured to allow components of the combustion analyzer to communicate with other components of the combustion installation (e.g. the valves as mentioned in FIG. 1) or with external devices (e.g. user interfaces).

Other 312 can include any other suitable devices or components useful in a combustion analyzer configured to sense, detect and/or measure gas concentrations in a combustion process. Other 312, for example can include one or more heaters and/or other heat supply components configured to provide and/or otherwise assist in the regulation and control of sensor(s) 308 (e.g. by heating up or reducing the heat of the sensor block(s)). In one example, heaters and/or other heat supply components can, based on a control signal from controller 304 for example, adjust the operating temperature of sensor(s) 308. In one example, other 312 can include a heater strut assembly, including, but not limited to, wiring, thermal switches, heater rods, insulators, heater clamps, thermocouples and any other suitable components and/or devices. In another example, other 312 can include a band heater. In another example, other 312 can include a ceramic fiber heater. In another example, other 312 can include any other suitable device(s) and/or components suitable to maintain and regulate the operating temperature of sensor(s) 308 and/or other elements of analyzer 300.

Although the present invention has been described with reference to preferred examples, workers skilled in the art will recognize that changes can be made in form and detail without departing from the spirit and scope of the invention. For example, the components of the systems and apparatuses can be integrated or separated. Moreover, the operations of the systems and apparatuses disclosed herein can be performed by more, fewer, or other components and the methods described can include more, fewer, or other steps. Additionally, steps can be performed in any suitable order.

What is claimed is:

1. A combustion analyzer comprising:
   an oxygen sensor configured to detect oxygen in a combustion process and generate a first sensor signal indicative of a concentration of oxygen;
   a dual carbon monoxide-methane sensor configured to operate at a temperature of 600° C. and provide a second sensor signal indicative of methane concentration and to operate at 300° C. to selectively provide a third sensor signal indicative of carbon monoxide concentration;
   wherein the combustion analyzer is configured to determine the concentration of oxygen based on the first sensor signal and generate a carbon Monoxide concentration output and a methane concentration output based on the dual carbon monoxide-methane sensor signals and the concentration of oxygen; and
   wherein a controller generates, based on the sensor signals, a control signal; and
   wherein the control signal is configured to bring the dual carbon monoxide-methane sensor to 300° C. and apply a carbon monoxide calibration algorithm when the concentration of oxygen is below a certain threshold, wherein the carbon monoxide calibration algorithm comprises changing a temperature of the dual carbon monoxide-methane sensor.

2. The combustion analyzer of claim 1, wherein the dual carbon monoxide-methane sensor comprises a calorimetric catalytic carbon monoxide sensor.

3. The combustion analyzer of claim 1, wherein the dual carbon monoxide-methane sensor is operated at 600° C. at startup.

4. The combustion analyzer of claim 1, wherein the control signal is configured to adjust flow of fuel or air to the combustion process.

5. The combustion analyzer of claim 1, wherein the control signal is configured to generate an alert.

6. The combustion analyzer of claim 1, wherein the threshold comprises a 10.0%-20.0% oxygen concentration range.

7. A method of improving the control of a combustion process comprising:
- heating a dual carbon monoxide-methane sensor to 600° C.;
- determining a concentration of oxygen in the combustion process using an oxygen sensor;
- comparing the oxygen concentration to a certain threshold;
- applying, when the oxygen concentration is a below the threshold, carbon monoxide calibration algorithm configured to allow the dual carbon monoxide-methane sensor to detect carbon monoxide within the combustion process and generate a sensor indicative of a concentration of carbon monoxide;
- applying, when the concentration is above the threshold, a methane calibration algorithm configured to allow the dual carbon monoxide-methane sensor to detect methane within the combustion process and generate a sensor signal indicative of concentration of methane; and
- generating a control signal based on the sensor signals.

8. The method of claim 7, wherein the threshold is 10.0% oxygen concentration.

9. The method of claim 7, wherein the threshold is 20.0% oxygen concentration.

10. The method of claim 7, wherein the control signal is configured to trigger an alert.

11. The method of claim 7, wherein the control signal is configured to adjust flow of air to the combustion process.

12. The method of claim 7, where in the control signal is configured to adjust flow of fuel to the combustion process.

13. The method of claim 7, wherein the carbon monoxide calibration algorithm is based on a calibration operation wherein the dual carbon monoxide-methane sensor is heated to 300° C. and exposed to known levels of carbon monoxide concentration.

14. The method of claim 13, wherein the known levels of carbon monoxide concentration is 1000 ppm.

15. The method of claim 7, wherein the methane calibration algorithm is based on a calibration operation wherein the dual carbon monoxide-methane sensor is heated to 600° C. and exposed to known levels of methane concentration.

16. The method of claim 15, wherein the known levels of methane concentration falls in a range of 0-5.0%.

17. A combustion analyzer comprising:
- an oxygen sensor configured to sense the presence of oxygen in a combustion process and generate a first sensor signal indicative of the concentration of oxygen in the combustion process;
- a dual carbon monoxide-methane sensor configured to sense the presence of carbon monoxide or methane in the combustion process and generate a second sensor signal indicative of a concentration of carbon monoxide or a concentration of methane in the combustion process; and a controller configured to determine the concentration of oxygen based on the first signal and compare it to a threshold, wherein the controller selectively generates a control signal, based on the comparison, to heat the dual carbon monoxide-methane sensor to 600° C.

18. A combustion analyzer comprising:
- an oxygen sensor configured to detect oxygen in a combustion process and generate a first sensor signal indicative of a concentration of oxygen;
- a dual carbon monoxide-methane sensor configured to operate at a temperature of 600° C. and provide a second sensor signal indicative of methane concentration and to operate at 300° C. to selectively provide a third sensor signal indicative of carbon monoxide concentration;
- wherein the combustion analyzer is configured to determine the concentration of oxygen based on the first sensor signal and generate a carbon monoxide concentration output and a methane concentration output based on the dual carbon monoxide-methane sensor signals and the concentration of oxygen; and
- wherein a controller generates, based on the sensor signals, a control signal; and
- wherein the control signal is configured to apply a methane calibration algorithm when the concentration of oxygen is above a certain threshold, wherein the methane calibration algorithm comprises changing a temperature of the dual carbon monoxide-methane sensor.

* * * * *